United States Patent
Telimaa et al.

[11] Patent Number: 5,970,806
[45] Date of Patent: *Oct. 26, 1999

[54] MULTI-CYLINDER PIPETTE

[75] Inventors: Juha Telimaa, Kyröläntie; Mauno Heinonen, Valliraitti; Kari Järvimäki, Haukitie; Jouko Mikkonen, Jousimiehentie, all of Finland

[73] Assignee: Labsystems OY, Helsinki, Finland

[ * ] Notice: This patent is subject to a terminal disclaimer.

[21] Appl. No.: 08/966,246

[22] Filed: Nov. 7, 1997

[30] Foreign Application Priority Data

Nov. 13, 1996 [FI] Finland ................................ 964549

[51] Int. Cl.$^6$ ........................................................ B01L 3/02
[52] U.S. Cl. ........................................................ 73/864.17
[58] Field of Search ............................ 73/863.32, 863.33, 73/864.17, 864.18; 422/100

[56] References Cited

U.S. PATENT DOCUMENTS

| | | |
|---|---|---|
| Re. 32,210 | 7/1986 | D'Autry . |
| 3,855,868 | 12/1974 | Sudvaniemi . |
| 3,991,617 | 11/1976 | D'Autry . |
| 4,215,092 | 7/1980 | Suovaniemi et al. . |

FOREIGN PATENT DOCUMENTS

| | | |
|---|---|---|
| 0 093 355 | 11/1983 | European Pat. Off. . |
| 0 112 887 | 7/1984 | European Pat. Off. . |
| 0 172 508 | 2/1985 | European Pat. Off. . |
| 0 172 508 | 2/1986 | European Pat. Off. . |
| 0 189 900 | 5/1996 | European Pat. Off. . |
| 52025 | 2/1977 | Finland . |
| 54238 | 7/1978 | Finland . |
| 73368 | 6/1987 | Finland . |
| 36 30 568 | 3/1987 | Germany . |
| 36 41 593 | 6/1987 | Germany . |
| 8-117618 | 5/1996 | Japan . |
| 1 392 791 | 4/1975 | United Kingdom . |

*Primary Examiner*—Robert Raevis
*Attorney, Agent, or Firm*—Oblon, Spivak, McClelland, Maier & Neustadt, P.C.

[57] ABSTRACT

The patent application discloses a multi-cylinder pipette (1). The pipette specifically comprises 16 4.5 mm spaced channels (5), being thus suitable for use with a plate comprising equally spaced 16×24 wells. The set of cylinders of the pipette has been assembled from separate elements. A set of cylinders composed of elements provides ease of manufacture. Moreover, the same element and other components can be assembled to provide various pipettes.

12 Claims, 4 Drawing Sheets

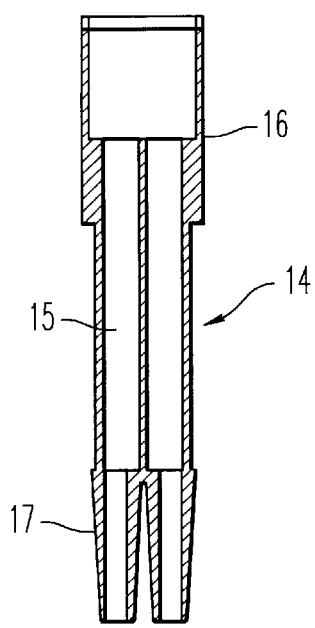
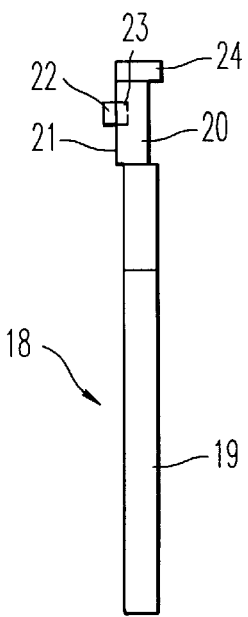
FIG. 3
FIG. 5
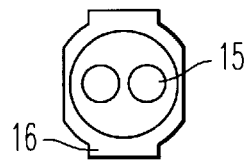
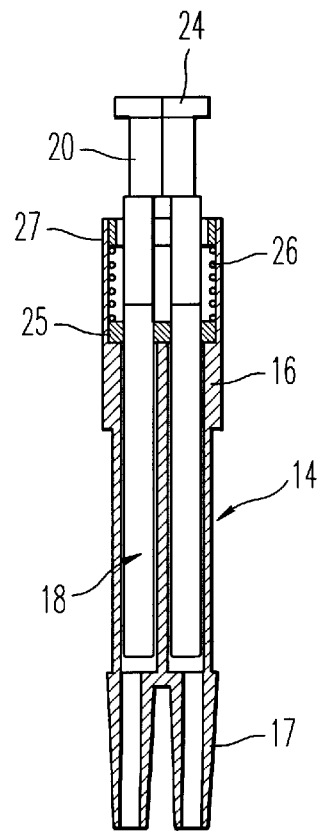
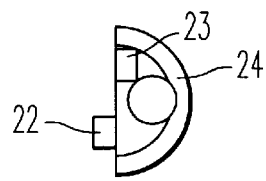
FIG. 4
FIG. 6
FIG. 7

MULTI-CYLINDER PIPETTE

FIELD OF TECHNOLOGY

The invention relates to laboratory technology and concerns a multi-tubular pipette, which can be used for instance for dispensing liquids simultaneously into an array of sample vessels arranged in a row.

TECHNOLOGICAL BACKGROUND

Multi-channel pipettes comprise a plurality of channels, into which liquid is sucked and from which it is simultaneously removed.

Multi-channel pipettes have been manufactured especially for devices called micro-titration plates, comprising 9 mm spaced 8×12 wells in a matrix. Multi-channel pipettes used alongside a microtitration plate usually comprise 8 or 12 channel, enabling liquid to be dispensed or removed in a single operation over an entire vertical or horizontal row. Also 4-channel pipettes have been used. FI patent specification 52025, for instance, discloses certain multi-channel pipettes. The sets of cylinders in currently used multi-channel pipettes are made in one piece by injection moulding from plastic.

In pipettes called step pipettes, the liquid absorbed into the container is removed in several small steps. Multi-channel step pipettes used together with microtitration plates are also known. These pipettes involve the problem of an awkwardly long piston stroke to allow for sufficient suction volume. Elliptic cylinder have been used with a view to shorten the piston stroke, as described in FI patent specification 73368. In elliptic pipette cylinders, sealing involves a problem.

DESCRIPTION OF THE INVENTION

General Description

A multi-cylinder pipette as defined in claim 1 has now been invented. The other claims define a number of preferred embodiments of the pipette.

In the pipette in accordance with the invention, the set of channels is composed of elements such that at least one element comprises at least two channels joined together. The manufacture of such a set of channels is easier than that of a single cylinder unit. Moreover, the dimensional variations of the cylinders are reduced. The same elements can also be assembled to form various sets of cylinders. Most preferably, the sets of cylinders are made by injection moulding from a plastic suitable for the purpose.

The invention is suitable for use for instance in multi-channel pipettes with a relatively large number of channels (e.g. 16 or 24) relatively closely (e.g. 4.5 mm) spaced.

The invention is also suitable for use in multi-channel pipettes requiring a relatively large suction volume compared to the distance between the channels.

DRAWINGS

The accompanying drawings pertain to the special description of the invention. In the drawings FIG. 1 shows a 16-channel pipette in accordance with the invention FIG. 2 shows the sample plate used together with the illustrated pipette FIG. 3 is a lateral view of the element for the set of cylinders FIG. 4 is a top view of the element of FIG. 3

FIG. 5 is a lateral view of a piston suitable for the element of FIG. 3

FIG. 6 is a top view of the piston of FIG. 5

FIG. 7 shows the element of FIG. 3 with the pistons of FIG. 5 inserted

DETAILED DESCRIPTION

In the pipette in accordance with the invention, the channels may be arranged in a row or in a matrix composed of several rows. It may comprise for instance 8, 12, 16 or 24 channels.

The pipette may also be electrically operated.

One element comprises one or more cylinders. The elements may be assembled to form various sets of cylinders.

Figure 1:
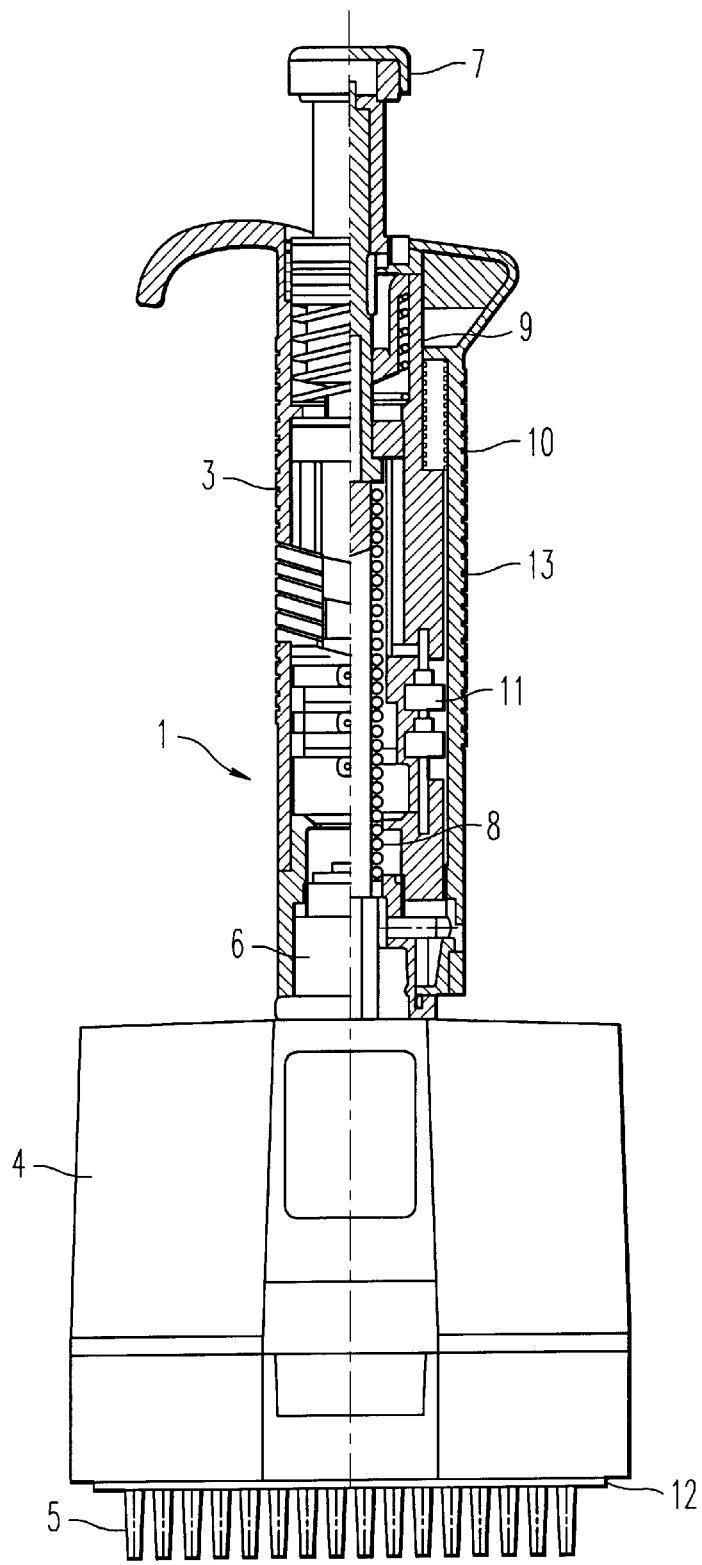
Figure 2:
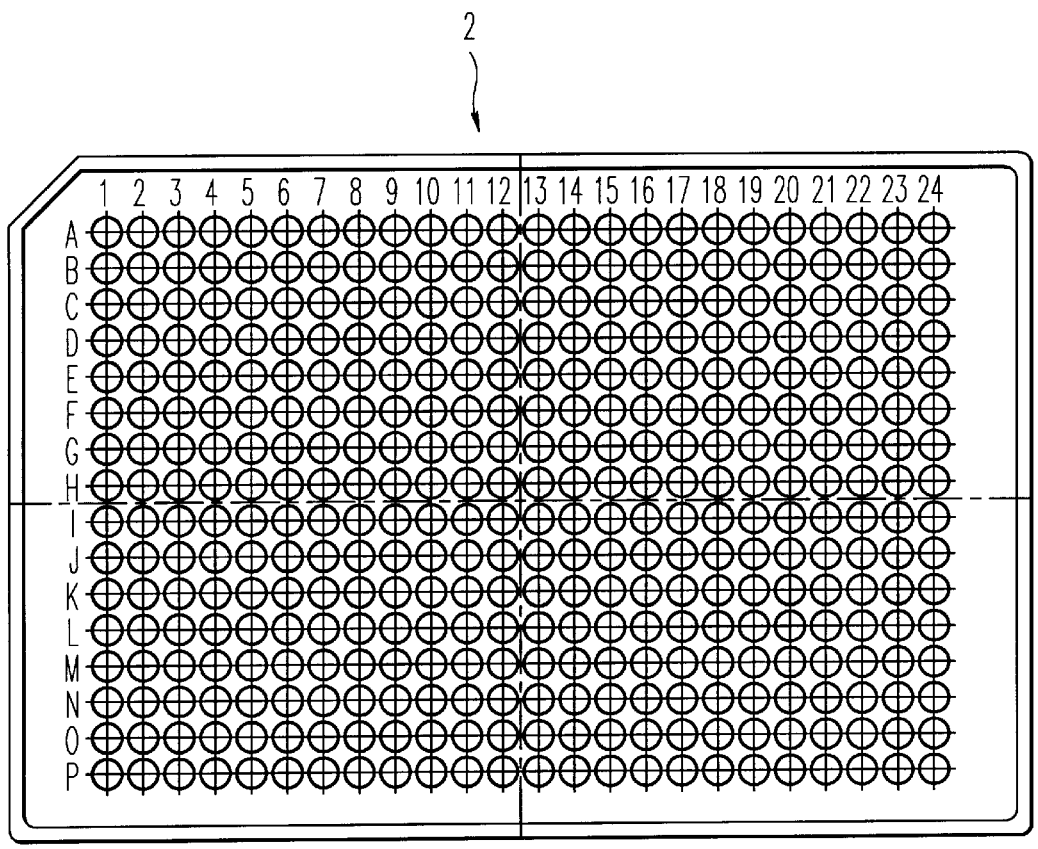

In FIG. 1, multi-channel pipette 1 is intended for use together with plate 2 of FIG. 2, comprising 4.5 mm spaced 16×24 wells (NANOPLATE™, Labsystems Oy). The pipette has a handle 3 and a body 4 at the lower end of the handle. The body comprises 16 channels 5 arranged in a row, and liquid containers are fixed to the lower ends of these.

Within the body, each channel comprises a cylinder including a piston. The pistons are fixed to a common cross-arm, from where a piston rod 6 is directed upwards into the handle, the piston rod having at its upper end a knob 7 extending above the handle. The pistons are most preferably fixed to their actuator with the intermediation of a spring, whose force is greater than the friction force between the piston and the cylinder and which allows for a slight lateral movement of the pistons (cf e.g. FI patent specification 47460, corresponding to U.S. Pat. No. 3,855,868).

In the handle, there is a primary spring 8 pressing the piston rod upwards and a stronger secondary spring 9, the rod being pressed against the force of the secondary spring after the primary movement, for the containers to be as completely emptied as possible. The piston stroke length in the primary step, and thus the suction volume is adjustable by turning a button connected to a volume control system. The control system comprises a bushing 10 rotatable with regard to the piston rod but non-rotatable with regard to the handle, and the handle comprises a stopper matching the upper surface of the bushing. The volume control is connected with a volume display 11 based on a digital ring series (cf. e.g. FI patent specification 64752, corresponding to EP patent specification 112887).

In addition, the pipette comprises a mechanism for removing the tip containers, including container pushers 12 and an associated spring-actuated arm 13 (cf. e.g. FR patent specification 2287941, corresponding to U.S. Pat. No. 3,991,617). The pusher may be actuated with a lever mechanism, thus reducing the force required for pressing.

The plate in FIG. 2 comprises 16 horizontal rows (A–P) and 24 vertical rows (1–24). The outer dimensions of the plate equal the dimensions of a conventional 8×12 microtitration plate.

The set of cylinders in the multi-channel pipette of FIG. 1 can be assembled from elements 14 in FIG. 3, each including two tubes 15. The elements are placed next to each other in a number corresponding to a desired even number of ducts. The pipette body 4 correspondingly includes appropriate means for retaining the joined elements in position. At its upper end, the element is provided with a larger common body member 16, from the bottom of which the adjoining cylinders are directed downwards. At the lower end of the cylinders, there are spaced tip members 17, into which the liquid containers are fitted. The mutually matching outer sides of the body members have a plane shape. The body members are dimensioned such that the distance between adjacent tubes in adjacent elements will equal the distance between the cylinders in an element.

Piston 18 in FIG. 5 has a piston member 19 fitting into cylinders 15 and a fastening member 20 at its upper end. The fastening member has a vertical counter-surface 21, located laterally outside the piston member. The fastening member is dimensioned such that, when two, pistons are positioned with their counter-surfaces facing each other, the distance between the piston axes will equal the distance between the cylinder axes.

Fastening member 20 may also comprise appropriate means for facilitating the positioning and joining of the pistons. To this end, one lateral half of counter-surface 21 is provided with a projection 22 and the other lateral half with a recess 23 matching the shape of the projection at a corresponding point. When the counter-surfaces are pressed against each other, the projection in the one piston will engage the recess in the other piston.

A semi-circular flange 24 is provided at the upper end of fastening member 20. When pressed against each other, the flanges form a fastening member, with which the couple of pistons is attached to the actuating arm common for the couples of pistons. In this way, the actuating arm may be identical to that of a pipette with half the number of ducts but double spacing.

FIG. 7 shows an element 14, into which pistons 18 have been inserted. At the bottom of the recess in body member 16, a common seal 25 is provided, having sliding surfaces sealed against the pistons. The seal is pressed against the bottom of the body member by a spring 26, which is fixed into position by means of a top ring 27.

Figure 8:
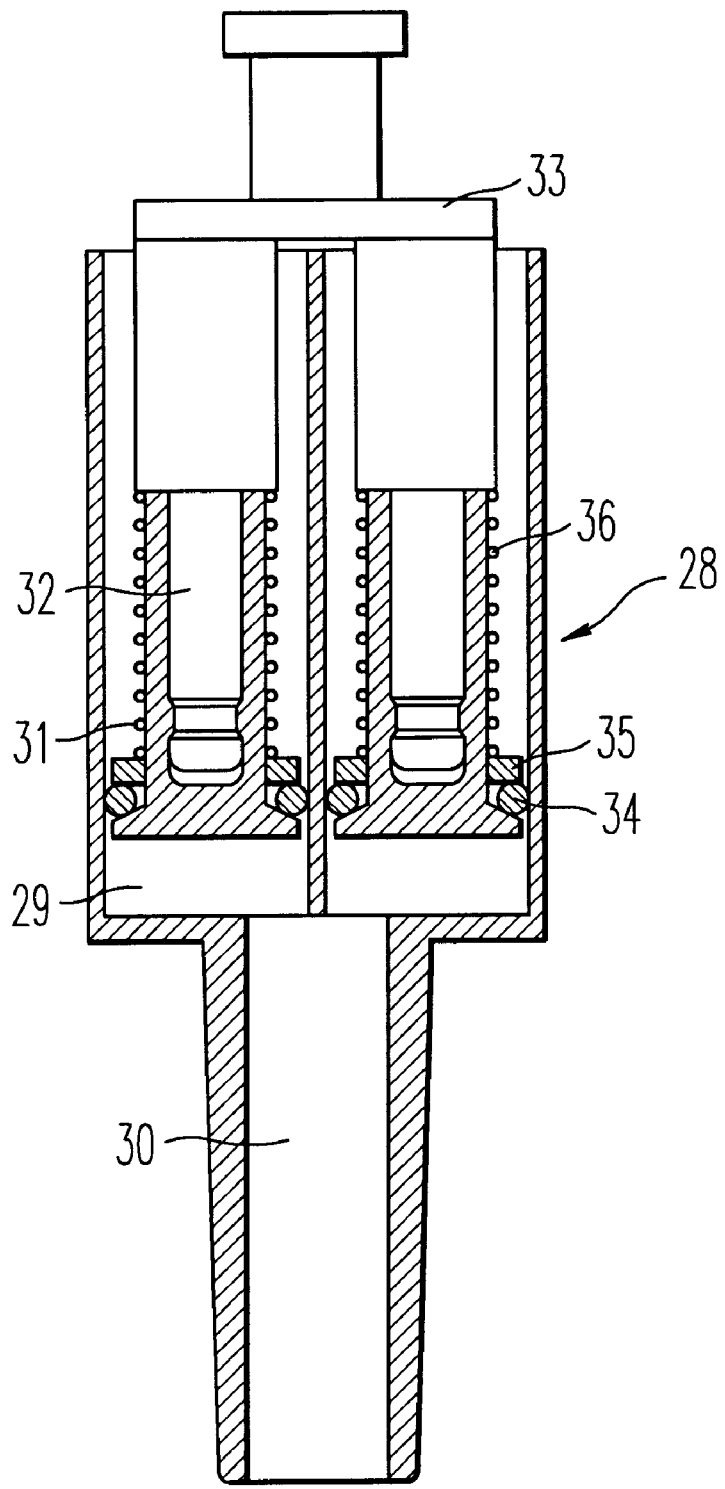
FIG. 8 shows a second cylinder element including a piston in accordance with the invention.

The cylinder element 28 of FIG. 8 comprises two joined circular tubes 29, each of which communicating at its lower end with the tip member 30 in the centre of the element. A tip container is fixed to the tip member. Both of the cylinders comprise a piston 31. Piston rods 32 are interconnected by means of a fork-like fastening means 33.

Piston 31 has a larger lower end with a downwardly slanting circular upper surface. This surface is provided with for sealing an O-ring 34, which is pressed down by means of a support ring 35 and a spring 36. The spring is pressed from above by the bushing of fastening member 33, which has a width greater than that of the piston rod.

The elements 28 of FIG. 8 can be assembled to form the set of cylinders of a multi-channel pipette by placing the elements next to each other with tips 30 in a row. In this way, the distance between the tips can be considerably reduced without the piston stroke required for sufficient suction volume gaining an awkward length. Still, circular cylinders provide ease of sealing.

We claim:

1. A multi-cylinder pipette, having a set of cylinders with at least three cylinders, each of said at least three cylinders including a piston, the actuation of which can generate suction or pressure in a tip channel connected with the cylinders, said set of cylinders comprising:

a multi-cylinder element comprising at least two cylinders of said at least three cylinders, said at least two cylinders being formed monolithically, said at least two cylinders not monolithically formed with a third cylinder of said at least three cylinders.

2. A pipette as claimed in claim 1, in which the cylinders in the multi-cylinder element are arranged in one row.

3. A pipette as claimed in claim 2, in which the multi-cylinder element consists of two cylinders.

4. A pipette as claimed in claim 1, wherein at least two pistons included in said at least two cylinders have been joined together with fastening means, said fastening means configured to be fastened to an actuator common for the pistons in the pipette.

5. A pipette as claimed in claim 4, in which the pistons have been joined together in couples.

6. A pipette as claimed in claim 5, wherein a first piston of said at least two pistons has a fastening member, which is fastened to a corresponding fastening member in a second piston of said at least two pistons.

7. A pipette as claimed in claim 1, in which the tip channels are arranged in one row.

8. A pipette as claimed in claim 1, in which each cylinder is connected with a specific tip channel.

9. A pipette as claimed in claim 1, in which a first tip channel is connected with several cylinders.

10. A pipette as claimed in claim 9, in which the tip channels are arranged in one row and in which a tip channel is connected with several tubes arranged in a row transverse to the row of tip channels.

11. A set of cylinders for a pipette, comprising at least three cylinders, each of which contains a piston, wherein the set of cylinders is composed of separate elements, at least one of which being a multi-cylinder element comprising at least two monolithically formed cylinders of said at least three cylinders not monolithically formed with a third cylinder of said at least three cylinders.

12. A set of cylinders for a pipette comprising at least three cylinders, wherein the set of cylinders is composed of separate elements, at least one of which being a multi-cylinder element comprising at least two monolithically formed cylinders of said at least three cylinders, said at least two cylinders not monolithically formed with a third cylinder of said at least three cylinders.

* * * * *

UNITED STATES PATENT AND TRADEMARK OFFICE
CERTIFICATE OF CORRECTION

PATENT NO. : 5,970,806

DATED : October 26, 1999

INVENTOR(S): Juha TELIMAA et al.

It is certified that an error appears in the above-identified patent and that said Letters Patent is hereby corrected as shown below:

On the title page, item [75], the Inventors' cities are incorrect. It should read as follows:

--[75] Inventors: Juha Telimaa, Järvenpää; Mauno Heinonen, Vantaa; Kari Järvimäki, Espoo; Jouko Mikkonen, Helsinki; all of Finland.--

On the title page, item [45], is incorrectly listed. It should read as follows:

--[45] Date of Patent: Oct. 26, 1999--

On the title page, the Terminal Disclaimer was erroneously listed. It should be deleted.

Signed and Sealed this

Twenty-sixth Day of December, 2000

Attest:

Q. TODD DICKINSON

*Attesting Officer*     *Director of Patents and Trademarks*